(12) United States Patent
Birkill et al.

(10) Patent No.: US 8,275,461 B2
(45) Date of Patent: Sep. 25, 2012

(54) PAIN RELIEVING WAVEFORM SYSTEM AND METHOD

(75) Inventors: Corlius Fourle Birkill, Rietondale (ZA); Roche van Rensburg, Pretoria (ZA)

(73) Assignee: Xavant Technology (ZA)

( * ) Notice: Subject to any disclaimer, the term of this patent is extended or adjusted under 35 U.S.C. 154(b) by 53 days.

(21) Appl. No.: 12/958,986

(22) Filed: Dec. 2, 2010

(65) Prior Publication Data

US 2012/0143281 A1    Jun. 7, 2012

(51) Int. Cl.
*A61N 1/00* (2006.01)

(52) U.S. Cl. ......................................................... 607/46

(58) Field of Classification Search ..................... 607/46
See application file for complete search history.

(56) References Cited

U.S. PATENT DOCUMENTS 4,232,680 A * 11/1980 Hudleson et al. ............... 607/46
5,628,768 A *  5/1997 Lubbe ............................. 607/46

* cited by examiner

*Primary Examiner* — George Manuel
(74) *Attorney, Agent, or Firm* — Ostrolenk Faber LLP

(57) ABSTRACT

A system and method for treating pain are disclosed. A voltage source provides an electric current, and a switching waveform controller receives the electric current and provides a first signal having a first waveform of a first frequency. A switching high frequency generator receives the electric current and provides a second signal having a waveform of a second frequency that is higher than the first frequency. A microprocessor controls the switching waveform controller and the switching high frequency generator. The second signal is superimposed on the first signal, providing a modified first signal. Alternatively, the switching waveform controller and the switching high frequency generator use one or more passive components and the second signal is superimposed on the first signal. At least one electrode receives the modified first signal, and the at least one electrode transmits a third signal associated with the modified first signal to a patient's skin.

19 Claims, 6 Drawing Sheets

PAIN RELIEVING WAVEFORM SYSTEM AND METHOD

BACKGROUND

1. Field

The present application relates, generally, to patient treatment and, more particularly, to pain treatment using electrical signals.

2. Description of the Related Art

Pain management remains a high concern for patients and medical caregivers alike. One known treatment for pain involves the use of electrical signals that are applied transcutaneously. Known in the art as transcutaneous electrical nerve stimulation, electrical stimulus in the form of electric signals are applied to the patient's skin. The signals effectively inhibit or otherwise suppress pain impulses from reaching the brain via the central nervous system.

Known transcutaneous electrical nerve stimulation devices involve the use of low frequency electrical signals to treat pain. For example, frequencies in the range of 2.5 to 60 kHz are typical for patient treatment.

Thus, systems for transcutaneous electrical nerve stimulation are known, including for stimulating nerves directly at a site, such as on muscle, or other areas of the body that impact or affect a patient's central nervous system.

SUMMARY

A system and method for treating pain are disclosed. A voltage source provides an electric current, and a switching waveform controller receives the electric current and provides a first signal having a first waveform of a first frequency. A switching high frequency generator also receives the electric current and provides a second signal having a waveform of a second frequency that is higher than the first frequency. In an embodiment, microprocessor controls the switching waveform controller and the switching high frequency generator to superimpose the second signal on the first signal to provide a modified first signal. At least one electrode receives the modified first signal, and the at least one electrode transmits a third signal associated with the modified first signal to a patient's skin.

In an embodiment, the switching waveform controller and the switching high frequency generator may be implemented using passive components. In this embodiment, a microprocessor, if any, does not control superimposing the second signal on the first signal.

Many other features and advantages of the present invention will become apparent from the following description of the invention that refers to the accompanying drawings.

BRIEF DESCRIPTION OF THE DRAWINGS

For the purpose of illustrating the invention, there is shown in the drawings a form which is presently preferred, it being understood, however, that the invention is not limited to the precise arrangements and instrumentalities shown. The features and advantages of the present invention will become apparent from the following description of the invention that refers to the accompanying drawings, in which.

DESCRIPTION OF EMBODIMENTS

The present application provides a system and method that utilizes a waveform for treating pain. The waveform includes a low frequency square wave with a high frequency bi-polar exponentially decaying waveform superimposed thereon. In at least one embodiment, the high frequency component provides electrical signals with a frequency of about 480 kHz. The waveform is used in conjunction with a nerve stimulation device and is applied transcutaneously, that is, externally and transmitted through the skin of the user to provide pain relief. In at least one embodiment, the square wave modification of such square waves includes a high frequency, bi-polar exponentially decaying component. Accordingly, a system and method are provided for treating pain as a function of a transcutaneous application of a stimulating waveform that includes a square wave with a high frequency bi-polar exponentially decaying component superimposed thereon.

In accordance with the present application, the square wave signal provides benefits for treatment of acute pain while the high frequency bi-polar exponentially decaying signal provides relief for chronic pain. One skilled in the art will recognize that the application of high frequency signals from outside the skin to relieve chronic pain is a significant departure from known prior pain management techniques.

Figure 1:
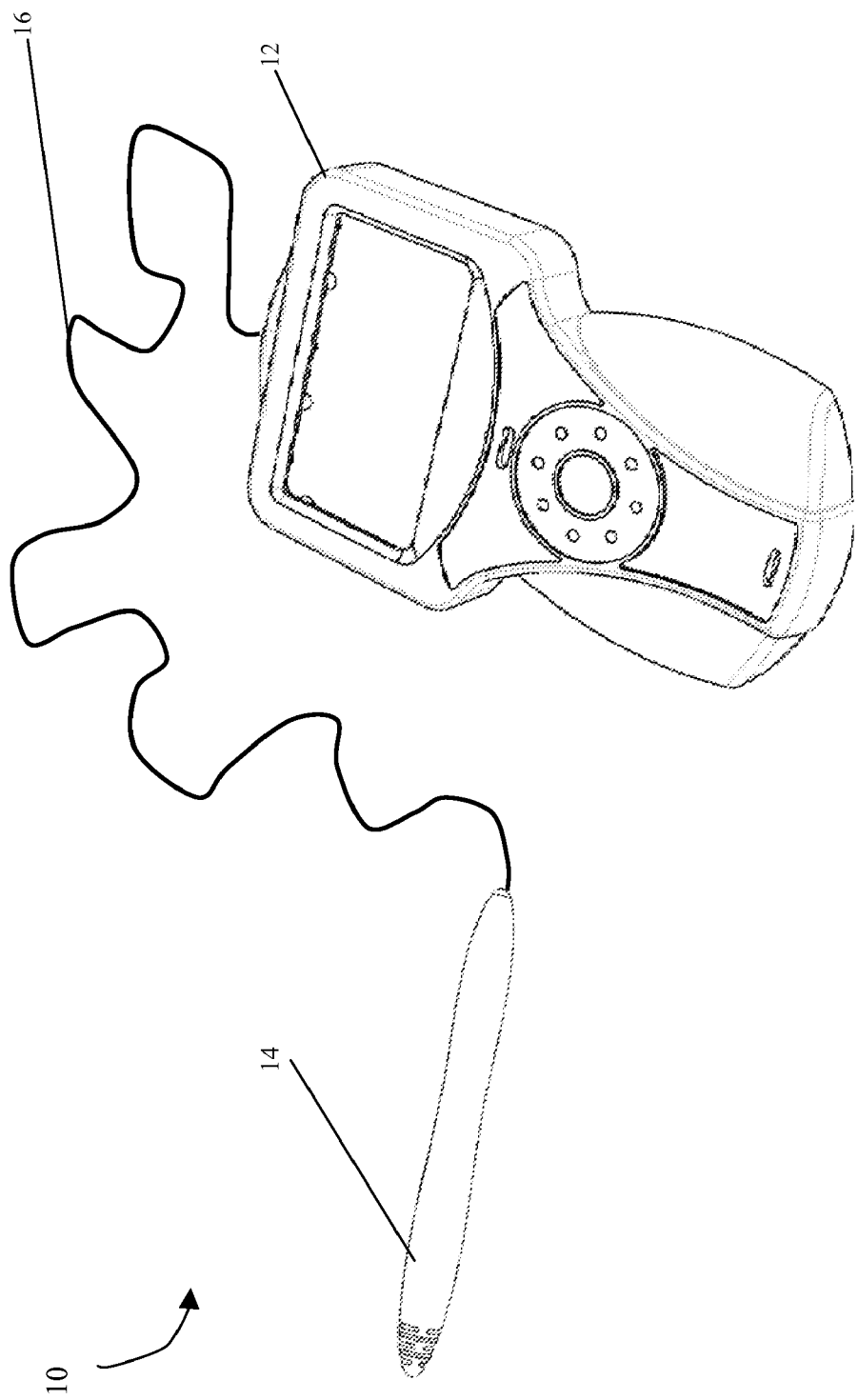
FIG. 1 illustrates an embodiment of a transcutaneous electrical stimulator pain relieving device in accordance with the present disclosure.

Referring now to the drawings, in which like reference numerals refer to like elements, FIG. 1 illustrates an embodiment of a transcutaneous electrical stimulator pain relieving device 10 in accordance with the present disclosure. As illustrated in the example shown in FIG. 1, device 10 includes controller 12 and electrical nerve stimulator wand 14. In the configuration shown in FIG. 1, wand 14 is coupled to controller 12 via cable 16, which carries one or more of digital and analog signals to wand 14, including for delivery of the waveform that includes a square wave with a high frequency bi-polar exponentially decaying component superimposed thereon. Of course, wand 14 may be coupled to controller 12 in other suitable ways, such as wirelessly, e.g., via radio frequency and/or infrared signals (not shown) and described in greater detail with reference to FIG. 3. Wand 14 acts as one electrode for the application of an electrical signal to the patient. While not explicitly shown, a second electrode, also electrically connected to controller 12 is provided.

Figure 2:
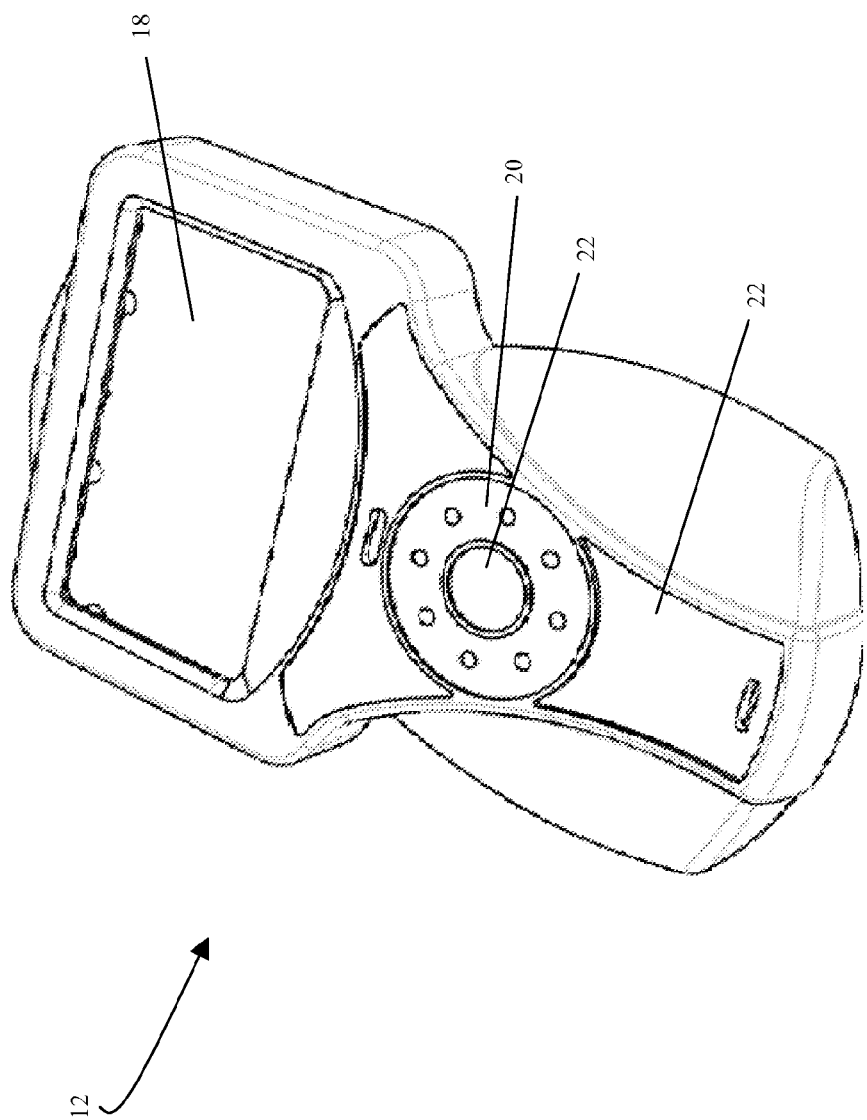
FIG. 2 illustrates a controller in accordance with an embodiment.

FIG. 2 illustrates a figure of controller 12 in accordance with an embodiment. Controller 12 preferably includes display screen 18, which is preferably configured as an liquid crystal display ("LCD"), but may configured as a CRT, LED, plasma or other suitable display. Preferably, operational controls are graphically displayed on display 18. In one embodiment, display screen 18 is a touch-screen, and selections of various controls are made by the user simply tapping or otherwise touching display 18. Alternatively or in addition, command selections may be made via control wheel 20, which may be rotatable and cause menu choices, command options or various graphical screen controls to be displayed on display 18. Moreover, pushbutton 22 may be pressed by a user to select a respective command, menu choice or other option provided on display 18. Of course various other designs may be provided with controller 12, such as rocker switches, rollerballs, touch pads or the like to enable operation by a user. Preferably, controller 12 includes battery compartment 22 to hold one or more batteries an provide power to controller 12. Any suitable power source, however, may be used.

Figure 3:
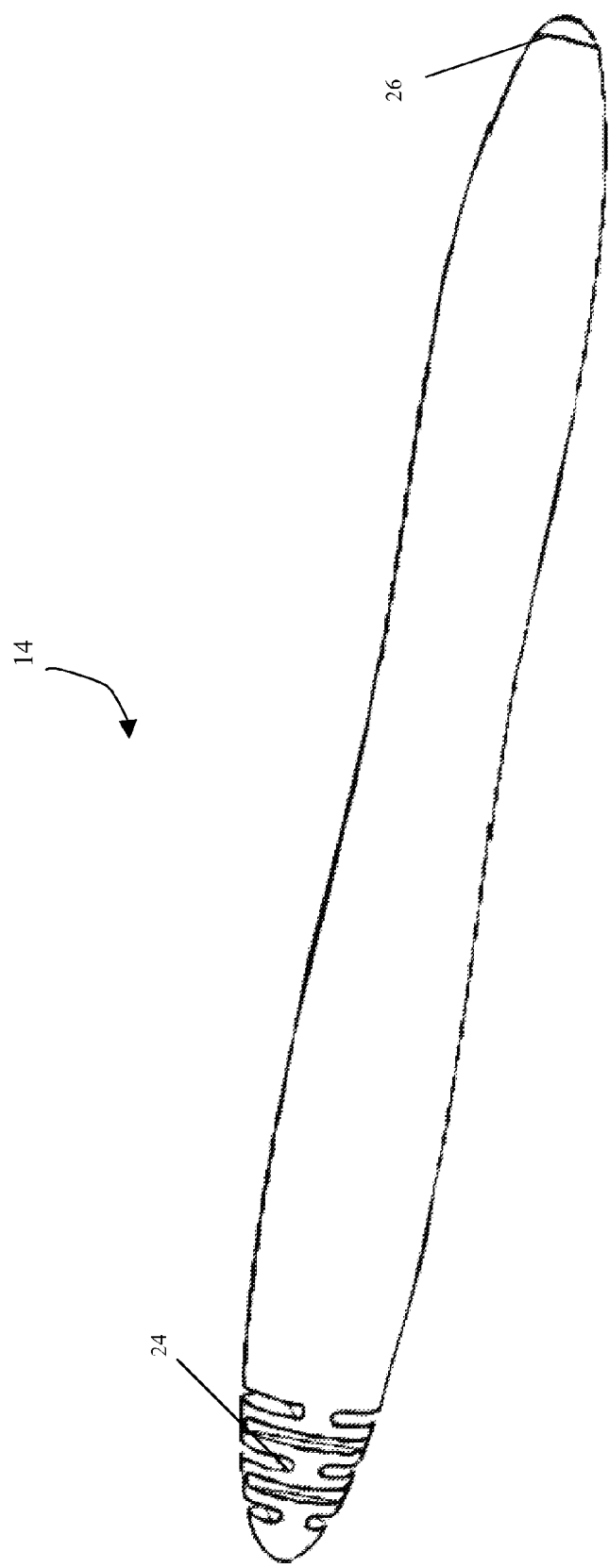
FIG. 3 illustrates a nerve stimulator wand 14 in accordance with an embodiment.

FIG. 3 illustrates a nerve stimulator wand 14 in accordance with an embodiment. Unlike the embodiment shown in FIG. 1, nerve stimulator wand 14 shown in FIG. 3 is wirelessly connected to controller 12. Wand 14 is suitably provided with one or more electrodes 26 that provide electrical stimulation at frequency ranges, substantially as disclosed herein. During operation, a gel, such as aloe vera gel or other substance, is applied to a patient's skin to promote or improve connectivity. Accordingly and in connection with the example transcutaneous electrical stimulator pain relieving device 10, a user actuates operation controls on controller 12 to cause wand 14 to output a waveform for treating pain, wherein the waveform includes a square wave with a high frequency bi-polar exponentially decaying waveform that is superimposed thereon. In the embodiment shown in FIG. 3, wand 14 is provided with wireless connectivity, such as via RF receiver element 24. Wand 14 that is provided with wireless connectivity preferably includes a power source, such as one or more batteries (not shown).

Figure 4:
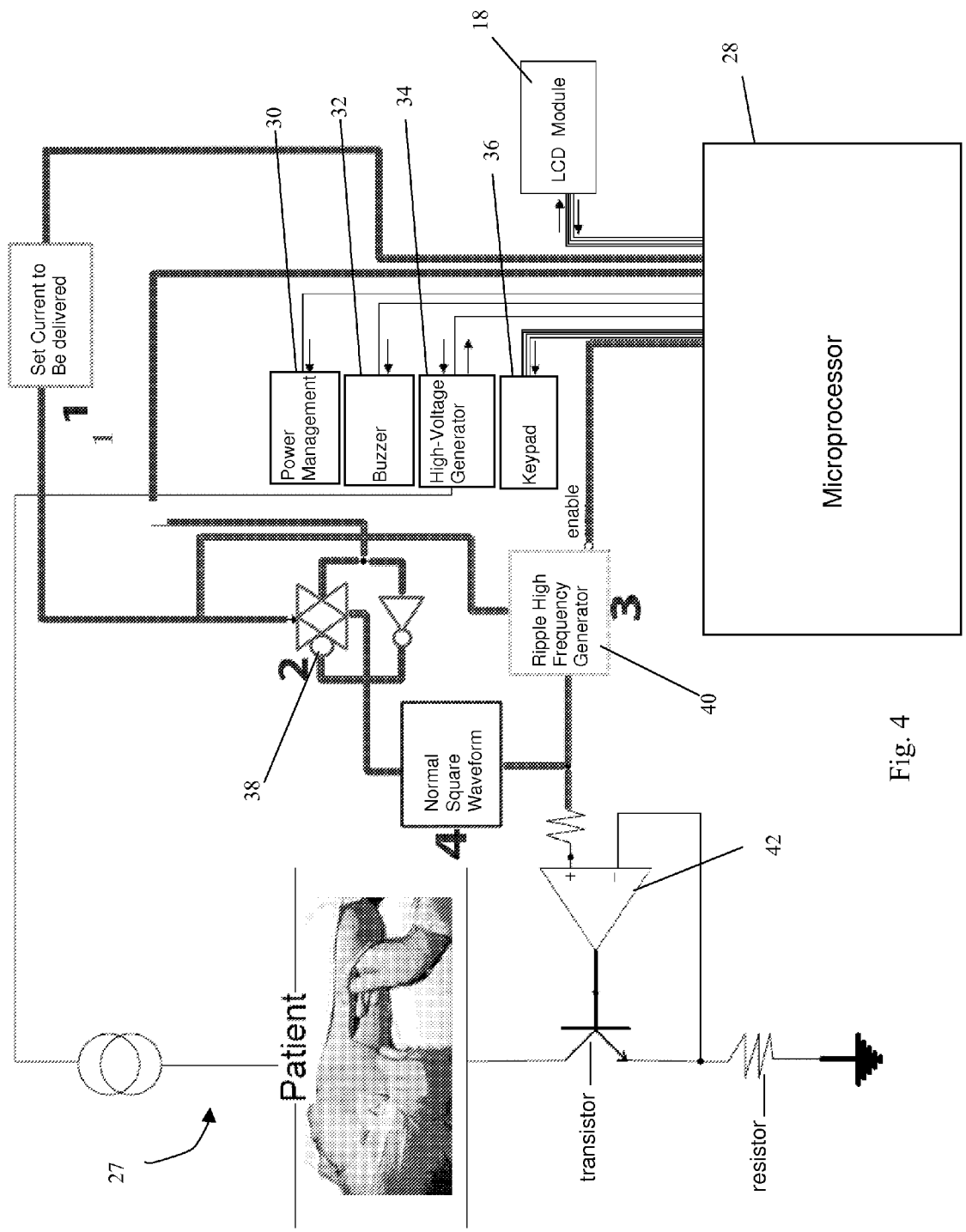
FIG. 4 illustrates an exemplary circuit for use in a transcutaneous electrical stimulator pain relieving device in accordance with an embodiment.

FIG. 4 illustrates an exemplary circuit 27 for use in the transcutaneous electrical stimulator pain relieving device 10. In the embodiment shown in FIG. 4, microprocessor 28 controls components set forth in controller 12, including in response to user-issued commands received therefrom. Microprocessor 28 preferably interfaces with power management module 30, audible ("buzzer") module 32, high-voltage generator 34, and keypad 36 set forth in controller 12, and is functionally integrated with LCD module 18. Commands issued by a user of controller 12, such as via LCD module 18, may set a current to be delivered. Alternatively, current levels may be preset.

Continuing with reference to FIG. 4, waveform controller 38, may be configured as an analogue switch that receives an analogue signal having a peak current set by the user (or reset). The analog signal is fed to generate a normal square waveform and a high frequency, bi-polar exponentially decaying waveform, via ripple high frequency generator 40. Waveform controller 38 preferably includes an enable pin for switching between the two possible modes i.e. "normal square waveform" or "oscillating superimposed on square waveform." As noted herein, the high frequency, bi-polar exponentially decaying waveform is superimposed on one or more peaks of the normal square wave, as described below. Continuing with reference to FIG. 4, the analogue signal is fed to operational amplifier 42, which provides a signal having a normal square wave, with its peak current set in accordance with instructions provided via the user. As noted herein, the normal square wave is modified to include a high frequency, bi-polar exponentially decaying component. In an embodiment, the analogue signal is conditioned such that the square waveform is superimposed with an oscillating function via ripple high frequency generator 40. Ripple high frequency generator 40 preferably includes an enable pin, which is set to active high.

In an alternative embodiment, the switching waveform controller and the switching high frequency generator may be implemented using passive components (not shown). In this embodiment, a microprocessor, if any, does not control superimposing the second signal on the first signal.

Continuing with reference to FIG. 4, high voltage generator 34 preferably steps up the voltage to create a high voltage, such as to a maximum of 400V. The amplitude of the waveform is anticipated at a maximum value, such as 30 milliamperes (mA), although higher maximum amperage is supported. 30 mA is a preferred value for maximizing patient endurance of treatment during periods of time. In an accordance with an embodiment, 400V enables delivering of 30 mA at a 13 kOhm load impedance. Typical known load impedance for percutaneous stimulation is approximately 5 kOhm. In accordance with one or more embodiments, the maximum is increased to 80 mA, provided the current is provided at load impedance, such as 5 kOhm.

The power requirements for the circuit 27 shown in FIG. 4 is a minimum of 3.3V. This can be supported by various known battery sizes and types, such as AA and AAA batteries.

Figure 5:
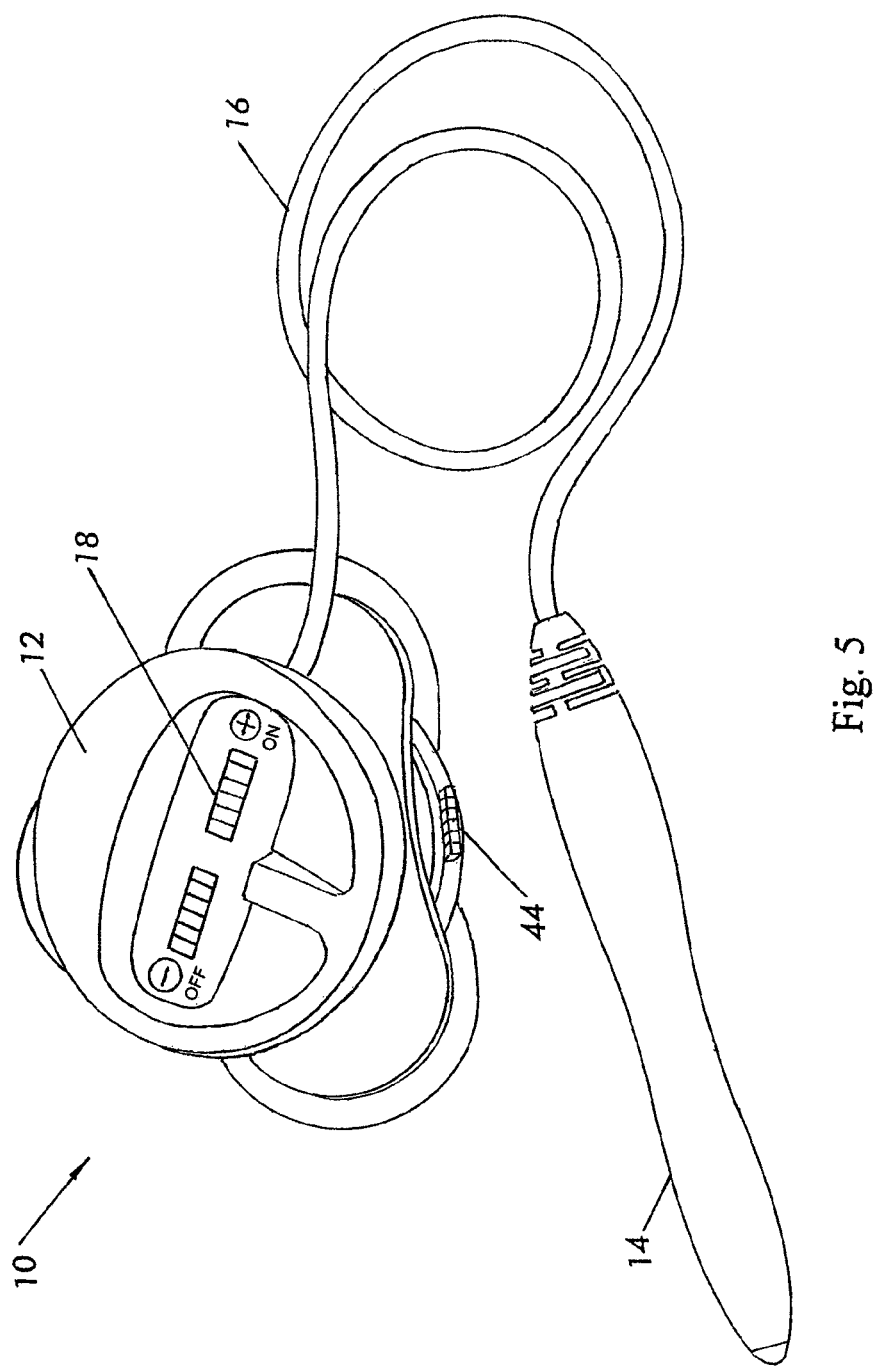
FIG. 5 illustrates an alternative embodiment of a transcutaneous electrical stimulator pain relieving device 10 in accordance with the present disclosure.

FIG. 5 illustrates an alternative embodiment of a transcutaneous electrical stimulator pain relieving device 10 in accordance with the present disclosure. In the example shown in FIG. 5, device 10 is configured to be coupled to a patient, and may include electrodes (not shown) that are provided below body section 44. In the example embodiment shown in FIG. 5, the wand 14 operates as one electrode and a second electrode is provided, for example, on or in controller 12. Thus, two electrodes are preferably included in the embodiment shown in FIG. 5, one being an anode one being a cathode, which enable a completed circuit. Further, device 10 illustrated in FIG. 5 may be disposable.

Figure 6:
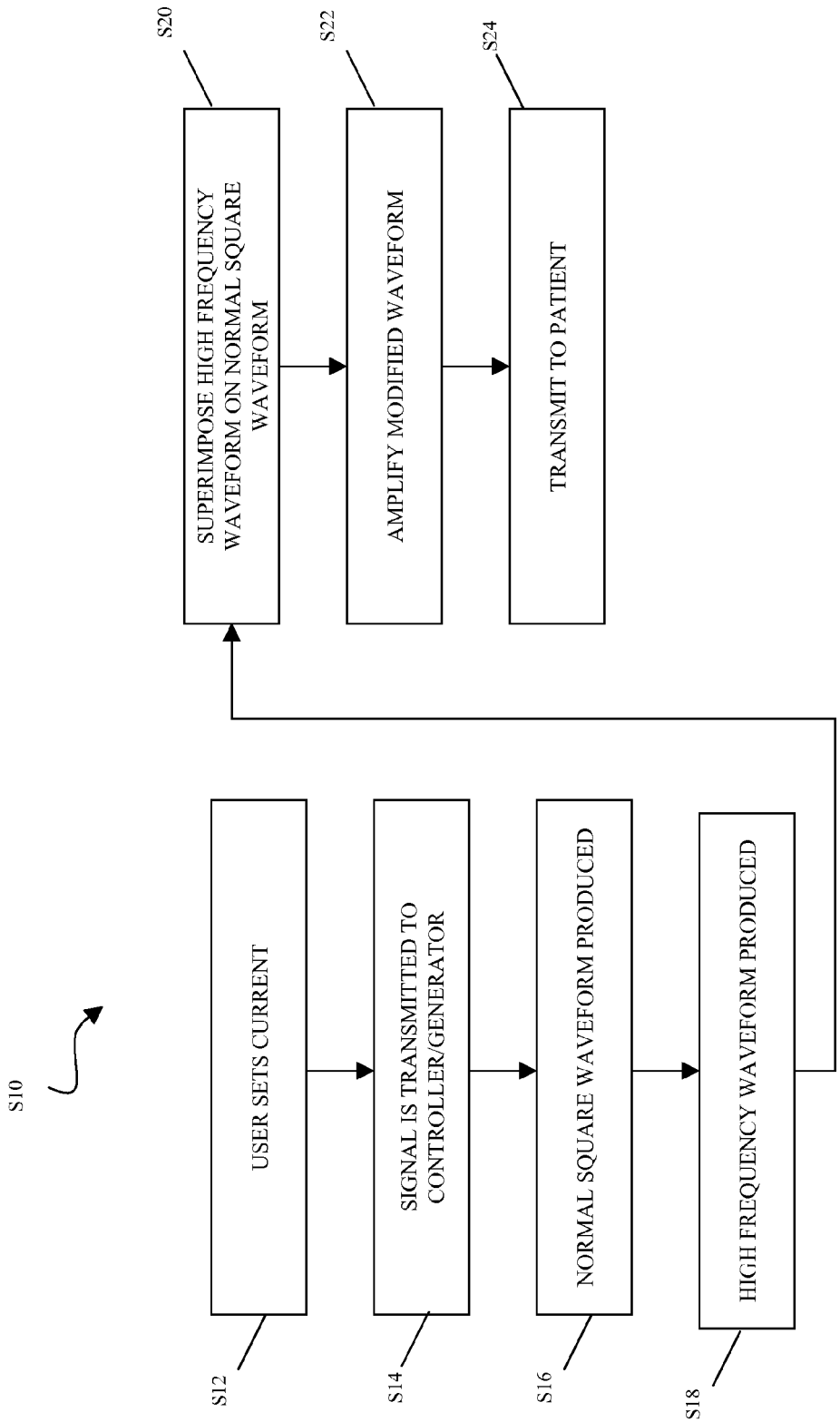
FIG. 6 is a flowchart illustrating steps associated with an example embodiment

FIG. 6 is a flowchart illustrating steps S10 associated with an example embodiment. At step S12, a user sets a current to be delivered. Thereafter, an analog signal is fed to waveform controller 38 and to ripple high frequency generator 40 (step S14). Waveform controller 38 provides a normal square waveform (step S16) and ripple high frequency generator 40 provides a high frequency, bi-polar exponentially decaying waveform (step S18). The high frequency, bi-polar exponentially decaying waveform is superimposed on the normal square waveform, for example at peaks of the square waveform, to provide a modified waveform (step S20). The modified waveform is amplified at step S22. At step S24, the modified waveform is provided to wand 14, and transmitted to the patient via electrodes 24.

In yet another embodiment, a functional transcutaneous electrical stimulator pain relieving device 10 is provided in a single, handheld wand. In this embodiment, one or more of metal contacts are provided on a handle section of the wand that may operate as the anode. One or more metal contacts are also provided on the tip of the wand, which may operate as the cathode. In this way, the device outputs the waveform that includes a square wave with a high frequency bi-polar exponentially decaying waveform that is superimposed thereon to a patient, for treating pain.

Although the present invention is described and shown in relation to particular embodiments thereof, many other variations and modifications and other uses will become apparent to those skilled in the art. Thus, various embodiments and variations are shown and described herein, and it is preferred, therefore, that the present invention be limited not by the specific disclosure herein.

What is claimed is:
1. A system for treating pain, the system comprising:
a voltage source providing an electric current;
a switching waveform controller that receives the electric current and provides a first signal having a first waveform of a first frequency;

a switching high frequency generator that receives the electric current and provides a second signal having a waveform of a second frequency that is higher than the first frequency;

a controller that controls the switching waveform controller and the switching high frequency generator to superimpose the second signal on the first signal to provide a modified first signal;

at least one electrode that receives the modified first signal, wherein the at least one electrode transmits a third signal associated with the modified first signal.

2. The system of claim 1, wherein second waveform is a bi-polar exponentially decaying waveform.

3. The system of claim 1, further comprising a user interface configured to receive a setting from a user for defining a peak current.

4. The system of claim 3, further comprising a display that provides the user interface.

5. The system of claim 4, wherein the display is at least one of a liquid crystal display, a cathode ray tube display, a plasma display and a light emitting diode display.

6. The system of claim 1, wherein the third signal is transmitted for a predetermined period of time.

7. The system of claim 1, wherein the first waveform is square waveform.

8. The system of claim 1, further comprising a high voltage generator configured to step up the voltage to a voltage higher than the voltage provided by the voltage source.

9. The system of claim 1, wherein the second signal is superimposed at peaks of the first waveform.

10. The system of claim 1, further including a wand that accommodates the at least one electrode.

11. The system of claim 1, wherein the wand receives the modified first signal wirelessly.

12. The system of claim 1 wherein the system is disposable.

13. The system of claim 1, wherein the second frequency is in the range of 100 kHz to 500 kHz.

14. The system of claim 1, wherein the third signal is the modified first signal.

15. The system of claim 1, wherein the controller is a microprocessor.

16. A method, the method comprising:
providing electric current having a peak setting;
delivering the current to a waveform controller to provide a first signal having a first waveform having a first frequency;
delivering the current to a high frequency generator to provide a second signal having a decaying waveform having a second frequency that is higher than the first frequency; and
superimposing the second signal on the first signal to provide a modified first signal.

17. The method of claim 16, further comprising:
delivering the modified first signal to at least one electrode;
applying the electrode and transmitting the modified first signal to a patient's skin.

18. A system for treating pain, the system comprising:
a voltage source providing an electric current;
a switching waveform controller that receives the electric current and provides a first signal having a first waveform of a first frequency;
a switching high frequency generator that receives the electric current and provides a second signal having a waveform of a second frequency that is higher than the first frequency;
a controller that controls the switching waveform controller and the switching high frequency generator to superimpose the second signal on the first signal to provide a modified first signal;
at least one electrode that transmits the modified first signal to treat the pain.

19. A system for treating pain, the system comprising:
a voltage source providing an electric current;
a switching waveform controller that receives the electric current and provides a first signal having a first waveform of a first frequency;
a switching high frequency generator that receives the electric current and provides a second signal having a waveform of a second frequency that is higher than the first frequency;
wherein the switching waveform controller and the switching high frequency generator operate to superimpose the second signal on the first signal to provide a modified first signal;
at least one electrode that receives the modified first signal, wherein the at least one electrode transmits the modified first signal to treat the pain.

* * * * *